United States Patent [19]
Li et al.

[11] Patent Number: 5,882,933
[45] Date of Patent: Mar. 16, 1999

[54] METHOD FOR DETERMINATION OF LEUKOCYTES AND HEMOGLOBIN CONCENTRATION IN BLOOD

[75] Inventors: Yi Li; Carole Young, both of Miami; Robert H. Raynor, Cooper City, all of Fla.

[73] Assignee: Coulter International Corp., Miami, Fla.

[21] Appl. No.: 898,000

[22] Filed: Jul. 25, 1997

Related U.S. Application Data

[63] Continuation-in-part of Ser. No. 488,630, Jun. 8, 1995, Pat. No. 5,686,308.

[51] Int. Cl.[6] .......................... G01N 33/48; G01N 33/72
[52] U.S. Cl. ................................. 436/63; 436/10; 436/17; 436/66; 436/164; 436/172; 436/174; 436/175; 436/176; 436/824; 436/534; 435/2; 435/7.1; 435/7.2; 435/7.24
[58] Field of Search ..................................... 436/8, 10, 15, 436/17, 63, 66, 164, 166, 172, 174, 175, 176, 805, 824, 534; 435/2, 7.1, 7.2, 7.21, 7.24, 29, 30, 34, 39

[56] References Cited

U.S. PATENT DOCUMENTS

| | | | |
|---|---|---|---|
| 4,185,964 | 1/1980 | Lancaster | 436/17 |
| 4,286,963 | 9/1981 | Ledis et al. | 436/63 |
| 4,485,175 | 11/1984 | Ledis et al. | 436/63 |
| 4,528,274 | 7/1985 | Carter et al. | 436/10 |
| 5,030,554 | 7/1991 | Quintana et al. | 435/2 |
| 5,116,539 | 5/1992 | Hamaguchi et al. | 252/408.1 |
| 5,125,737 | 6/1992 | Rodriguez et al. | 356/39 |
| 5,155,044 | 10/1992 | Ledis et al. | 436/17 |
| 5,188,935 | 2/1993 | Leif et al. | 435/7.24 |
| 5,242,832 | 9/1993 | Sakata | 436/17 |
| 5,250,437 | 10/1993 | Toda et al. | 436/10 |
| 5,389,549 | 2/1995 | Hamaguchi | 436/10 |
| 5,437,985 | 8/1995 | Quintana et al. | 435/7.24 |
| 5,451,525 | 9/1995 | Shenkin et al. | 436/63 |
| 5,516,695 | 5/1996 | Kim et al. | 436/17 |
| 5,686,308 | 11/1997 | Li et al. | 436/63 |
| 5,731,206 | 3/1998 | Ledis et al. | 436/17 |

FOREIGN PATENT DOCUMENTS 325 710  4/1995  European Pat. Off. .

*Primary Examiner*—Maureen M. Wallenhorst
*Attorney, Agent, or Firm*—Mitchell E. Alter

[57] ABSTRACT

A method is provided for differentiating leukocyte subpopulations, immunophenotyping of lymphocytes and counting white blood cells. The method preserves leukocyte morphology and surface markers without using fixatives. In addition, the method finds utility in determination of hemoglobin concentration without using cyanide. The stable hemoglobin chromogen formed is measured at approximately 540 nm.

17 Claims, 18 Drawing Sheets

METHOD FOR DETERMINATION OF LEUKOCYTES AND HEMOGLOBIN CONCENTRATION IN BLOOD

CROSS REFERENCE TO RELATED APPLICATION

This application is a continuation-in-part of patent application Ser. No. 08/488,630, filed Jun. 8, 1995, now U.S. Pat. No. 5,686,308 issued on Nov. 11, 1997.

FIELD OF THE INVENTION

The present invention relates to a method to enable a determination of leukocyte subpopulations in a blood cell sample by means of suitable electronic instrumentation. In addition, the present invention relates to a determination of hemoglobin concentration in said blood sample.

BACKGROUND OF THE INVENTION

Analysis of leukocyte subpopulations from whole blood samples is an integral and essential part of diagnostic procedures regarding a multiplicity of pathologies. The ability to analyze the major subpopulations of leukocytes in an automated manner is essential for a rapid diagnosis of a single blood sample and for the rapid processing of many samples at once. In addition, the determination of hemoglobin concentration provides useful diagnostic information about the health of a patient.

Traditional diagnosis of blood samples involves the smearing of a blood sample on a microscope slide, followed by manual visual analysis of the individual slide. This approach is extremely time-consuming as well as being subjective to the interpretation of the individual analyzing the slide. These factors have led to the development of automated leukocyte analysis utilizing flow cytometry. In automated leukocyte analysis using hematology instruments, the red blood cells are lysed which enables the differentiation of the leukocytes and determination of hemoglobin concentration.

U.S. Pat. No. 4,286,963 (to Ledis et al.) describes a method for achieving rapid hemolysis of red blood cells in whole blood and automated analysis of lymphoid and myeloid subpopulations of leukocytes, and quantitative determination of hemoglobin using potassium cyanide.

U.S. Pat. No. 4,485,175 (to Ledis et al.) describes a method for performing differential determinations of leukocytes into three (3) subpopulations utilizing automated cell counting equipment. However, this method is limited to effect differentiation of the leukocytes into three subpopulations: lymphocytes, monocytes and granulocytes.

These above-mentioned methods not only lyse red blood cells, but also destroy leukocyte membranes. The differentiation, consequently, is based on the nuclear volumes of the leukocyte subpopulations. The application of these methods, alone or in combination with other means, prohibits further refinement in the diagnostic process of various disease states based on the differences in the immunochemical response of the surface marker of the cell membrane.

U.S. Pat. No. 5,155,044 (to Ledis et al.) discloses a method for isolation and analysis of leukocytes from a whole blood sample, which enables automated differentiation of leukocytes into five (5) subpopulations utilizing an automated hematology analyzer. However, this method cannot convert oxyhemoglobin of the sample to a stable chromogen for hemoglobin measurement. The oxyhemoglobin method is an unreliable method because of incomplete hemoglobin conversion.

U.S. Pat. No. 5,389,549 (to Hamaguchi et al.) describes a lysis reagent system which contains a nonionic polyoxyethylene surfactant. Using the method and lysis reagent system disclosed, it is difficult to do a full analysis of the five major leukocyte subpopulations. Full analysis of leukocyte subpopulations requires differential lysis of the red blood cells and leukocytes, and three separate determinations for the identity of eosinophil, neutrophil and basophil populations in addition to the lymphocyte and monocyte populations. Additionally, this system requires a hypotonic lysing environment which is extremely shocking to the cells and makes preservation of the cells in a near native state difficult.

In addition, measuring hemoglobin concentration in a blood sample is another diagnostic tool when doing blood analysis. Historically, hemoglobin determinations have been performed by forming and measuring cyanide hemoglobin. However, the reagent waste from this method is of enormous environmental concern. Several cyanide-free methods for lysing red blood cells and measuring hemoglobin have been developed. U.S. Pat. No. 5,250,437 (to Toda et al.) and U.S. Pat. No. 5,242,832 (to Sakata) all utilize quaternary ammonium salt lysis systems for hemolyzing red blood cells and oxidizing the hemoglobin. However, because of the harshness of the quaternary ammonium ion based systems on leukocytes, these systems cannot be used for combined leukocyte subpopulation differentiation greater than three subpopulations and hemoglobin determination, particularly if near native state, leukocyte differentiation is desired.

EPO No. 0 325 710 (to Hamaguchi et al.) discloses a method for the hemolysis of red blood cells. However, with this method, one can only differentiate three subpopulations in addition to measuring the oxyhemoglobin.

U.S. Pat. No. 5,516,695 (to Kim et al.) discloses a method for rapid analysis of a whole blood sample allowing the determination of five subpopulations of white blood cells, nucleated red blood cells, and lymphocyte immunophenotyping on automated hematology instrumentation. The disclosed method lyses red blood cells and concurrently fixes white blood cells and preserves surface antigens on lymphocytes. The preservation of white cell surface marker is based on fixation by an aliphatic aldehyde, which is known as an environmentally unfriendly chemical. In addition, the method requires heating of the reagent to about 40° C. for leukocyte differential of a whole blood sample in order to achieve the performance and the throughput requirement of an automated hematology analyzer. Without heating, the lysing time is substantially longer.

U.S. Pat. Nos. 5,030,554 and 5,437,985 (to Quintana et al.) disclose a method to prepare a whole blood sample for photo-optical analysis of lymphocyte subpopulations. The method comprises a 3-step sample preparation of: (1) lysing red cells with an acid lyse; (2) quenching the lysing reagent by an alkaline quench solution; (3) fixing white cells with a fixative solution. Indicator binding can be accomplished before, concurrent with, and after the lysing. This method also utilizes aldehyde fixation to preserve white cells. In addition, the light scatter and fluorescence analyses as disclosed differentiate only three leukocyte subpopulations, i.e., monocytes, lymphocytes and granulocytes.

SUMMARY OF THE INVENTION

In view of the foregoing, one object of the present invention is to provide a method for counting WBC, determining hemoglobin concentration, and differentiating at least four subpopulations of leukocytes in a blood cell sample. The method comprises exposing a blood cell sample to a lytic reagent for a time sufficient to lyse red blood cells without heating said exposed blood cell sample; adding a non-aldehyde stabilizing reagent to said exposed blood sample, wherein said stabilizing reagent inhibits further lytic action and stabilizes leukocytes without fixing the cells; analyzing said stabilized sample in less than 30 seconds after addition of the lytic reagent, wherein the mode of analysis is selected from at least two modes selected from DC, RF, and light scatter, wherein said analyzing is for counting WBC, and differentiating at least four leukocyte subpopulations selected from lymphocytes, monocytes, basophils, neutrophils and eosinophils; measuring light absorbance of the said stabilized sample at about 540 nm; and reporting WBC, hemoglobin concentration and at least four leukocyte subpopulations.

Another object of the present invention is to provide a method for stromatolysis of red blood cells in a blood cell sample, analysis of leukocyte subpopulations and lymphocyte subpopulations, and determining hemoglobin concentration in the blood cell sample. The method comprises incubating a blood sample with a fluorochrome-conjugated antibody; exposing of the incubated blood sample to a lytic reagent for a time sufficient to lyse red blood cells without heating said exposed blood cell sample; adding a non-aldehyde stabilizing reagent to said exposed blood sample, wherein said stabilizing reagent inhibits further lytic action and stabilizes leukocytes of the said blood sample in hypertonic medium ranging from about 400 mOsm to about 600 mOsm without fixing the cells; analyzing said stabilized sample in less than 30 seconds after addition of the lytic reagent, wherein the mode of analysis is selected from at least two modes selected from DC, RF, light scatter and fluorescence, wherein said analyzing is for differentiating leukocyte subpopulations; measuring light absorbance of said stabilized sample at about 540 nm; reporting leukocyte subpopulations in said blood cell sample; and reporting hemoglobin concentration of said blood cell sample.

A further object of the present invention is to provide a method for stromatolysis of red blood cells in a blood cell sample, analysis of leukocyte subpopulations and lymphocyte subpopulations, and determining hemoglobin concentration in the blood cell sample. The method comprises incubating a blood sample with antibody-conjugated latex particles; exposing the incubated blood sample to a lytic reagent for a time sufficient to lyse red blood cells; adding a non-aldehyde stabilizing reagent to said exposed blood sample, wherein said stabilizing reagent inhibits further lytic action and stabilizes leukocytes of the said blood sample without fixing the cells; analyzing the said stabilized blood sample in less than 30 seconds after addition of the lytic reagent, wherein the mode of analysis is selected from at least two modes selected from DC, RF, and light scatter, wherein said analyzing is for differentiating leukocyte subpopulations; measuring light absorbance of said stabilized sample at about 540 nm; reporting leukocyte subpopulations in said blood cell sample; and reporting hemoglobin concentration of said blood cell sample.

As will be better appreciated from the ensuing Detailed Description of the Preferred Embodiments, the invention is particularly advantageous vis-a-vis the prior art discussed above in that the invention provides a method which preserves cell surface morphology and enables lymphocyte immunophenotyping in addition to differentiation of leukocyte subpopulations. Another advantage of the present method is that it provides an automated hemoglobin concentration determination in conjunction with the above referenced differentiation and immunophenotyping. The invention and its various advantages will be better understood from the ensuing detailed description of preferred embodiments.

DETAILED DESCRIPTION OF THE PREFERRED EMBODIMENTS

Figure 1:
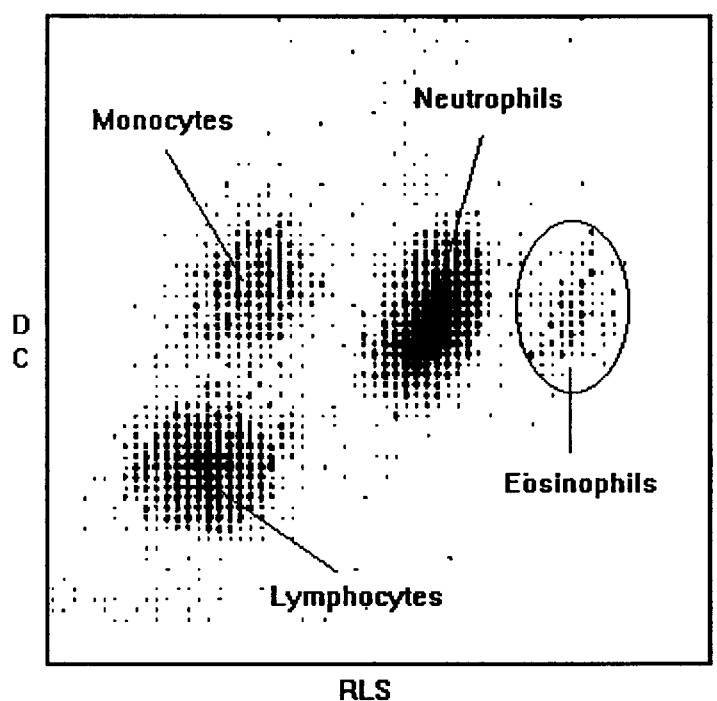
FIGS. 1–10 and 15–16 are scattergrams obtained in accordance with the practice of the present invention as described in Examples III, IV, V and VI.

1) Method for Stromatolysis of Red Blood Cells and Automated Differentiation of Leukocyte Subpopulations A blood sample can be obtained from a patient by conventional phlebotomy techniques. Typically used anticoagulant agents, including heparin, EDTA, acid citrate dextrose (ACD) and sodium citrate do not affect the performance of the present invention.

Subsequent to gathering, the blood sample is briefly mixed with a lytic reagent composition. The lytic reagent composition effectively stromatolyses red blood cells without detrimentally affecting leukocytes for subsequent analysis. The amount of time of exposing the blood sample to the lytic reagent composition prior to addition of a stabilizing reagent composition is important for the differentiation of leukocyte subpopulations presented by this invention. This exposure period should not exceed ten seconds, and is preferably less than seven seconds. The exposure time is specified for ambient temperatures (18° to 28° C.). This fast lytic activity preserves the leukocytes in near native conditions by avoiding prolonged exposure to the lytic reagent. For the purposes of this disclosure, near native condition means that cellular morphology is preserved so that analysis of the cellular subpopulations can be performed using histochemical or fluorescent labelling of cell surface markers.

A unique feature of the present method is that red blood cell lysis can be performed at ambient temperatures and it does not require heating of the mixed sample.

After the exposure to the lytic reagent composition, an appropriate amount of a non-aldehyde stabilizing reagent composition is added into the mixed sample and the cells are analyzed within about 20 seconds after addition of the non-aldehyde stabilizing reagent composition. Another unique feature of the present method is the use of a non-aldehyde stabilizing reagent composition which functions to inhibit lytic activity and prevent swelling of leukocytes so that the leukocytes are preserved for automated analysis, including differentiation of leukocytes and immunophenotyping of the lymphocytes.

The leukocyte fraction of the whole blood sample, treated by the above procedure, can be readily differentiated into at least two subpopulations of leukocytes. Preferably at least three subpopulations and more preferably at least four subpopulations and most preferably at least five subpopulations are differentiated, which include neutrophils, lymphocytes, monocytes, eosinophils and basophils. It has been found that four subpopulations, and more preferably five subpopulations, of leukocytes can be differentiated after exposure of a blood sample to the lytic reagent system using a single step measurement utilizing combined DC, RF and light scatter based on the subpopulations' respective abilities to cause a shift in the impedance of an electric field, such a shift being proportional to the cell volume; abilities to impede a radio frequency (RF) current and abilities to scatter light.

For the purposes of this disclosure, a lytic reagent composition and stabilizing reagent composition form a lytic reagent system. In addition, for purposes of this disclosure, a single step measurement means that a single aliquot of blood can be used with the same lytic reagent system to obtain a differentiation of a lymphocyte subpopulation with at least one other subpopulation of leukocytes consisting of eosinophils, basophils and neutrophils. Preferably, this differentiation is measured in less than 30 seconds and more preferably less than 20 seconds after the addition of the lytic reagent composition. Previous lysis reagent systems permitted only two parameter analyses in a given analysis step. Thus, to fully obtain a profile of five leukocyte subpopulations, a complex method of three individual determinations on the same sample followed by a combined analysis of the determinations was required.

The modes of analysis used for the differentiation of leukocytes by an automated hematology analyzer are generally described in U.S. Pat. No. 5,125,737, to Rodriguez et al., which is hereby incorporated by reference in its entirety.

Figure 2:
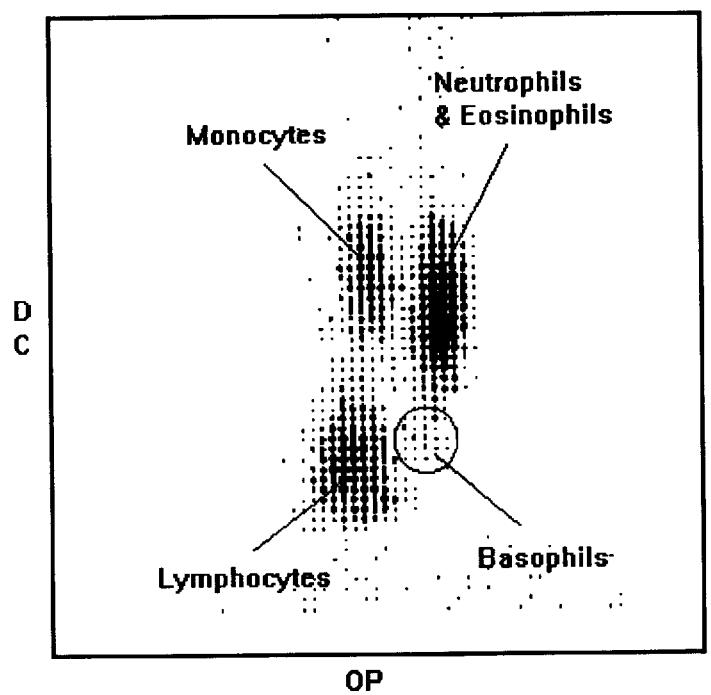

Although the present method is described in detailed terms using an analysis being conducted with combined DC, RF and LS measurements, it is within the contemplation of this invention to use at least two modes of analysis selected from the group consisting of DC, RF, LS, fluorescence and combinations thereof. It is within the further contemplation of this invention to use just two modes of analysis selected from the group consisting of DC, RF, LS and fluorescence. The results of such mode of analysis can be seen from the figures wherein DC versus Opacity (a function of RF and DC) is shown in FIG. 2; and DC versus LS is shown in FIG. 1. As appreciated by one skilled in the art, the mode of analysis can be only DC, which would result in at least two populations of leukocytes.

The method of the present invention provides the advantage of operating entirely at room temperatures, 18° to 28° C. Previous methods operated at an elevated temperature, 30° C. or higher, for adequate separation of eosinophils and basophils. This elevated temperature requirement necessitated analysis instrumentation which was significantly more complex, as the reactions must be thermostatically controlled. The present invention overcomes this need for thermostatic control by operating optimally at room temperature.

2) Method for Hemoglobin Determination

More than 300 abnormal hemoglobins have been discovered upon examination of patients with clinical symptoms and by electrophoretic surveys of a clinically normal population. Many of these abnormalities result in clinical pathologies having altered hemoglobin levels or hemoglobin having an altered ability to bind oxygen. Among these diseases are sickle cell anemia, both I- and J-thalassemias and hemoglobin M; Stamatoyannopoulos G. et al. (Eds), *Molecular Basis of Blood Disorders* (1986).

An ability to measure hemoglobin concentration in blood samples is an essential part of diagnostic analysis and is also important for monitoring responsiveness to therapies directed towards diseases which affect hemoglobin and to therapies which are directed towards other diseases but which may have adverse side effects on the hemoglobin level. The present invention allows for the analysis of at least three, preferably four, and more preferably five subpopulations of leukocytes in conjunction with a determination of hemoglobin concentration.

Lysis of red blood cells with the lytic reagent composition causes the release of hemoglobin as oxyhemoglobin. Addition of the stabilizing reagent composition results in the formation of a stable chromogen which has a maximum absorbance peak at 540 nm and a shoulder at 570 nm. The present method provides several advantages over the methods of hemoglobin measurement of the prior art. Unlike the previous methods, the present invention allows for the differentiation and analysis of leukocyte subpopulations in their near native state along with a determination of the hemoglobin concentration. In addition, the method provides for converting oxyhemoglobin to a stable hemoglobin chromogen in less than 10 seconds which allows for rapid automated analysis. The chromogen once formed is stable for up to 20 minutes.

3) Method for differentiating leukocyte subpopulations and lymphocyte immunophenotyping As discussed previously, because the method of the present invention preserves cellular morphology and cell surface markers, further analysis of lymphocyte subpopulations, i.e., various T and B cells, can be performed with appropriate surface marker labeling. Usually, cell surface markers can be labeled by a indicator, such as fluorochrome-conjugated antibodies, fluorescence dyes, and antibody-conjugated particles by incubation or staining. For instance, labeling of cell surface antigens with various fluorochrome-conjugated antibodies allows for lymphocyte immunophenotyping on conventional flow cytometers using the method of the present invention.

Example X shows an example of differentiation of CD8 positive lymphocytes using the method of the present invention on a fluorescence flow cytometer. Currently, commercial fluorescence flow cytometers require a separate sample preparation prior to transferring the sample to a flow cytometer for analysis. The method of the present invention can be used in a flow cytometer in an automatic mode because of the rapid speed and simplicity of the process.

Commercial fluorescence flow cytometers utilize photo-optical measurements, which typically measure forward and side light scatters and fluorescence signals. The flow cytometers are routinely used for lymphocyte immunophenotyping. However, their capability in leukocyte differential is usually limited to a 3-part differential, i.e., monocytes, lymphocytes and granulocytes. In addition, since multiple steps of sample preparation are usually required prior to analysis, cell concentrations after such pre-treatments no longer correlate to their original concentrations in the blood. Therefore, only percentages of leukocyte subpopulations are reported from the instrument, and not an absolute count of an interested cell type of the blood sample. Consequently, red blood cell count, white blood cell count, and leukocyte differentials are measured in hematology analyzers or blood counters.

On the other hand, most hematology methods use a lytic reagent for lysing red blood cells that is harsh to the leukocytes, because the lytic reagent either rips off the cell membrane or damages the cell membrane to a degree necessary to achieve differentiation of different cell types. The methods which use these lytic reagents are not compatible with immunophenotyping because of their inability to preserve cell surface markers. Therefore, hematology and immunology analyses of a blood sample are routinely performed on two different instruments, i.e., a hematology analyzer and a fluorescence flow cytometer, and most likely in two different clinical laboratories.

The present method provides a unique opportunity to combine leukocyte differential analysis with lymphocyte immunophenotyping, especially for the most commonly desired T and B cell types. This method can be performed in a single instrument in an automated mode. Since no additional cell separation and pre-treatments are needed using the method of the present invention, one can obtain both an absolute count of total white blood cells (WBC) and absolute count of leukocyte subpopulations when a known volume of a blood sample and known volumes of reagents are delivered.

Another advantage of the present method is preservation of leukocyte morphology and cell surface markers without using a fixative. Traditionally, blood sample preparations for immunophenotyping involve multiple steps of cell separation, washing, fixing and resuspending in an appropriate medium. It is known from the literature that cell damage or loss of a particular cell type is common after such lengthy sample preparation. Moreover, as previously discussed, obtaining absolute count for WBC and leukocyte subpopulations becomes impossible unless other secondary means are employed, such as introducing reference particles as taught by Shenkin, et al. in U.S. Pat. No. 5,451,525.

Recently, no-wash sample processes have evolved and cell damages have been reduced. However, these methods either include a fixing step to suspend the treated leukocytes in a fixative medium, or using fixatives in the lytic reagent to fix leukocytes during the lysis of the red blood cells. Common fixatives such as aldehydes are toxic. Although aldehydes are effective in preserving cell surface markers, the waste generated from hematology analyzers using aldehyde containing reagents cause environmental concerns. The method of the present invention selectively lyses red blood cells and preserves leukocyte cell morphology and surface markers without fixing the cells. Compared to conventional sample preparation methods and reagents, the method of the present invention is rapid, simple, and especially suitable for use on automated hematology analyzers and flow cytometers in an automated mode.

Example XI shows an alternative mode of lymphocyte subpopulation analysis by using non-fluorescence electro-optical analysis. CD4 positive lymphocytes (CD4+) are labeled with antibody-conjugated latex particles. The labeled blood sample is treated by the method of the present invention as described in Example XI, the CD4+ cells are differentiated by their shifted light scatter signals. The analysis is performed on a hematology analyzer equipped with DC, RF and light scatter measurement devices for differentiating leukocytes using the same lytic reagent system. The CD4 analysis is performed by switching from a 5-part differential analysis mode to a CD4 and CD8 lymphocyte analysis mode. The same reagent volumes and reaction times are used for both analysis modes. This example further illustrates the ability of the method of the present invention for further analysis of lymphocyte subpopulations.

4) Description Of Lytic Reagent System

One lytic reagent composition that is suitable in the above described method comprises an ethoxylated long chain amine compound and an acid to adjust the pH of the composition.

The ethoxylated long chain amine compound has a lipophilic tail and a branched hydrophilic, polar head group and can be represented by the formula:

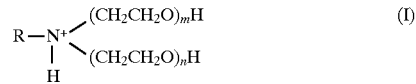

wherein R is an alky, alkenyl or alkynyl having 12 to 22 carbon atoms; m and n are each 1 or more, and m+n is 20 to 40. In the above structure, R is preferably 14 to 20 carbon atoms and m and n can be the same or different numbers.

The ethoxylated long chain amine compound of formula (I) can be synthesized by procedures known in the art as described, for example, in Porter, M. R., *Handbook of Surfactants*, Chapman & Hall, NY, pp. 147–150 (1991). When synthesized by the known procedure, m and n in the above formula should have approximately equal values. However, m and n need not have the same values.

The concentration of the ethoxylated long chain amine compound in the lytic reagent composition needs to be in an amount sufficient to selectively hemolyze the red blood cells in a whole blood sample, while leaving the remaining leukocytes essentially intact. The concentration of the ethoxylated long chain amine compound in the lytic reagent composition has been found to be effective in a broad range from about 8 g/L to about 80 g/L, preferably 12 g/L to 50 g/L.

The acid is used in an amount sufficient to adjust the pH of the lytic reagent composition in the range of approximately 2.0 to 3.6. The acid will usually be an effective amount of an organic acid. Preferably, formic acid or an effective mixture of formic acid with another organic acid or an inorganic acid is used. The organic acid to be used in admixture with the formic acid can be, for example, acetic, citric, oxalic, glycolic or propionic acid or a mixture of two or more of the aforementioned acids. Inorganic acids which can be mixed with the formic acid include, but are not limited to, hydrochloric, sulfuric and phosphoric acid.

The stabilizing reagent composition is added subsequent to red blood cell lysis to inhibit further lytic activity. Another unique feature of the present method is the use of a non-aldehyde stabilizing reagent composition. The non-aldehyde stabilizing reagent composition functions to neutralize the acid in the blood mixture and prevent swelling of leukocytes so that the leukocytes are preserved for the purposes of automated analysis, including differentiation of leukocytes and immunophenotyping of lymphocytes.

The stabilizing reagent composition is an aqueous buffered salt solution comprised of a simple physiological salt or salts. The salt or salts used in the stabilizing reagent composition can be a mixture of chloride salts and sulfate salts. The chloride salt can be, but is not limited to, sodium chloride or potassium chloride in a concentration of about 0.25 to 4% based on the total weight of the stabilizing reagent composition. The sulfate salt can be, but is not limited to, sodium sulfate or potassium sulfate in a concentration of about 0.25 to 9% based on the total weight of the stabilizing reagent composition. The stabilizing reagent composition is hypertonic and can have an osmolality of about 950 to 1800 mOsm. The salt concentration which affects the osmolality of the stabilizing reagent composition can vary because the volume of the stabilizing reagent composition can be adjusted relative to the lytic reagent volume so that the final osmolality of the blood sample mixture is between approximately 400 to 600 mOsm, preferably 410 to 520 mOsm.

The buffer may be any physiological buffer including, but not limited to, potassium or sodium carbonate, potassium or sodium phosphate, Tris, and potassium or sodium tetraborate. The pH of the stabilizing reagent composition is an approximate pH of 7 to 12.5, preferably having a pH of 9 to 11.5.

Optionally, one or more additive can be included in the lytic reagent system in concentrations that their presence is compatible with the primary functional components of the lytic reagent system. Among these additives are solubilizers and preservatives.

For the blood sample mixture, to achieve the best separation among the leukocyte subpopulations, a slight hypertonic condition is preferred, instead of a physiologically isotonic environment. The hypertonic environment created by the stabilizing reagent composition by its high physiological salt content prevents the swelling of the leukocytes that would result from their exposure to the lytic reagent composition and prevents the cell damages due to such swelling. In fact, a slight cell shrinkage occurs upon interaction with the stabilizing reagent for a few seconds, which produces a more confined cell distribution among the leukocyte subpopulations.

Unlike traditional lysing methods, a hypotonic environment is not required by the current method for the lysing of red blood cells. In the preferred embodiment, the addition of the stabilizing reagent composition converts the test sample to a slightly hypertonic environment which does not produce a dramatic osmotic stress to the leukocytes. The hypertonic environment ranges from 400 to 600 mOsm. The method of this invention results in a much tighter distribution within each subpopulation and a superior population separation when compared to the performances of prior art methods.

The leukocytes of aged and abnormal blood samples are usually fragile or sensitive to lysing conditions and are difficult to analyze by automated blood analyzers. The harshness of most lysis reagent systems, particularly acid based lysis systems, precludes their use for analysis of any but fresh blood samples, as the cells become too fragile as they age. The advantage of the present method for preventing leukocyte damage not only allows for differential analysis of freshly collected blood samples, but also for analysis of blood samples several hours after sample collection and also abnormal blood samples.

Another advantageous feature of this invention is its utility for differential analysis of other fluid samples, such as bone marrow, and blood samples of non-human species.

EXAMPLE I

Lytic Reagent Composition a) A first lytic reagent composition has been formulated with the following composition:

A cationic ethoxylated long chain amine compound with formula:

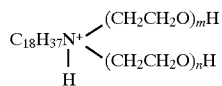

where m+n has a value of 30, was dissolved in deionized water at a concentration of 20 g/L. Formic acid was used to adjust the pH to 3.2. In addition, the following preservatives were added: 0.2 g/L EDTA, 0.5 g/L Proclin 300 (Rohm & Haas Co.), and 0.05 g/L 2,6-Di-tert-butyl-4-methylphenol.

b) A second lytic reagent composition has been formulated with the following composition:

A cationic ethoxylated long chain amine compound with formula:

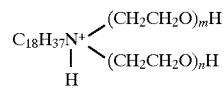

where m+n has a value of 25, was dissolved in deionized water at a concentration of 18 g/L. 10 g/L Pluronic 25R8 (BASF) was added as a solubilizer and 1.6 ml/L Formic acid was used to adjust the pH to 3.2.

c) A third lytic reagent composition has been formulated with the following composition:

A cationic ethoxylated long chain amine compound with formula:

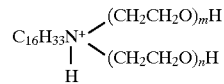

where m+n has a value of 30, was dissolved in deionized water at a concentration of 20 g/L. 5 g/L of Pluronic F38 (BASF) was added as a solubilizer and 1.6 ml/L of formic acid was used to adjust the pH to 3.2. In addition, the following preservatives were added: 0.2 g/L EDTA, 0.5 g/L Proclin 300 (Rohm & Haas Co.), and 0.05 g/L 2,6-Di-4-tert-butyl-4-methylphenol.

EXAMPLE II

Stabilizing Reagent Composition a) Carbonate Buffer Based Stabilizing Reagent Composition A first stabilizing reagent composition has been formulated which is comprised of 14 g/L of NaCl, 32 g/L of $Na_2SO4$, and 6.6 g/L of $Na_2CO_3$ buffer, pH adjusted to 11.0. The osmolality of this reagent is about 1080 mOsm.

b) Phosphate Buffer Based Stabilizing Reagent

A second stabilizing reagent has been formulated and contains 8.3 g/L $Na_2HPO_4$, 12.2 g/L $Na_3PO_4$, 14.3 g/L NaCl and 31 g/L $Na_2SO_4$, pH adjusted to 11. The osmolality of this reagent is about 1190 mOsm.

EXAMPLE III

Lysis of RBC and Differentiation of Normal Human Leukocyte Populations

A lytic reagent system prepared in deionized water from reagent grade chemicals and ethoxylated long chain amine compounds of industrial purity.

a) 20 g of the cationic ethoxylated long chain amine compound described in Example I a) was dissolved in 1 L of water. The pH of the ethoxylated long chain amine compound solution was adjusted to 3.2 by formic acid. 0.2 g of EDTA and 0.5 g of Proclin 300 (Rohm and Haas Co.) were added as antioxidant and anti-microbial preservatives, respectively. To 31 μl of a whole blood sample, 560 μl of the lytic reagent composition was added and the mixture was gently mixed by swirling for 4 seconds at room temperature (approximately 21° C.).

Figure 3:
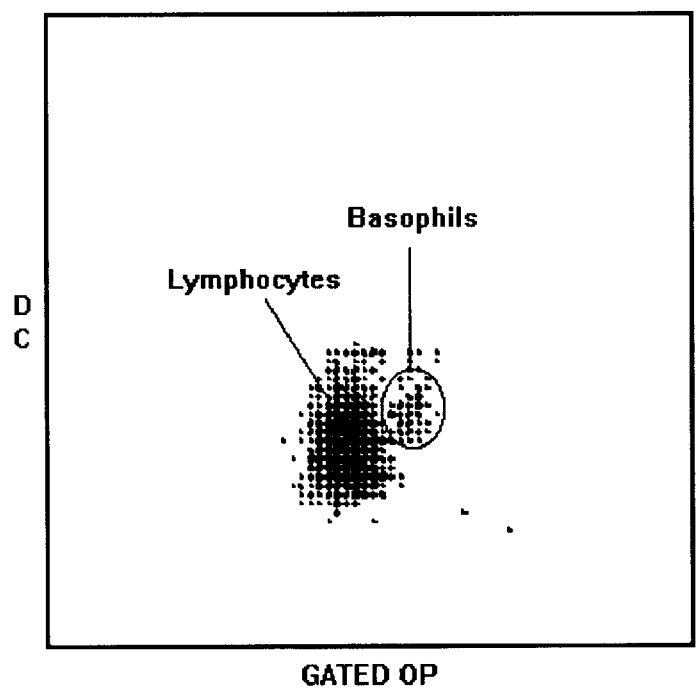

The lysing reaction was retarded by addition 230 μl of an aqueous stabilizing reagent composition containing 14 g/L of NaCl, 32 g/L of $Na_2SO_4$ and 6.6 g/L of $Na_2CO_3$, pH 11.0. The blood mixture was gently mixed and ready for differential analysis 15 seconds after the addition of the stabilizing reagent. The final blood mixture was kept at neutral pH (about 7) and in hypertonic condition with a osmolality about 445 mOsm. Three-dimensional differential analysis was conducted on a COULTER® STKS hematology analyzer with DC, RF and light scatter measurements utilizing a focus flow technique and ISOTON® III diluent as a sheath fluid. The resulting scattergrams are illustrated in FIG. 1 and FIG. 2. Four distinct subpopulations of leukocytes were identified and quantified in the DC vs. rotated light scatter (RLS) scattergram, FIG. 1. FIG. 2 illustrates the separated leukocyte subpopulations in the scattergram of DC vs. Opacity (a function of RF and DC). A fifth subpopulation of the leukocyte, basophils, is isolated by gating out other overlapping subpopulations in the DC vs. Opacity scattergram. The isolated basophil population is depicted in the scattergram illustrated in FIG. 3.

Figure 14:
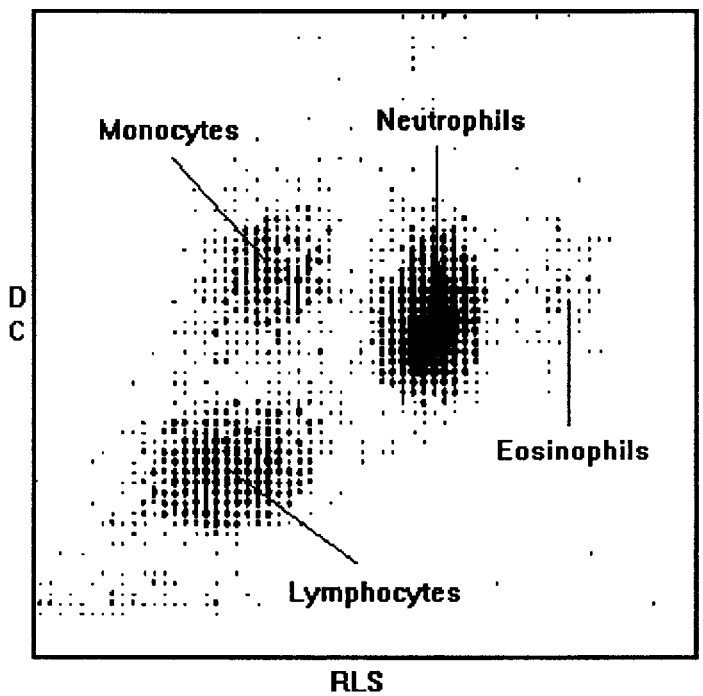
Figure 15:
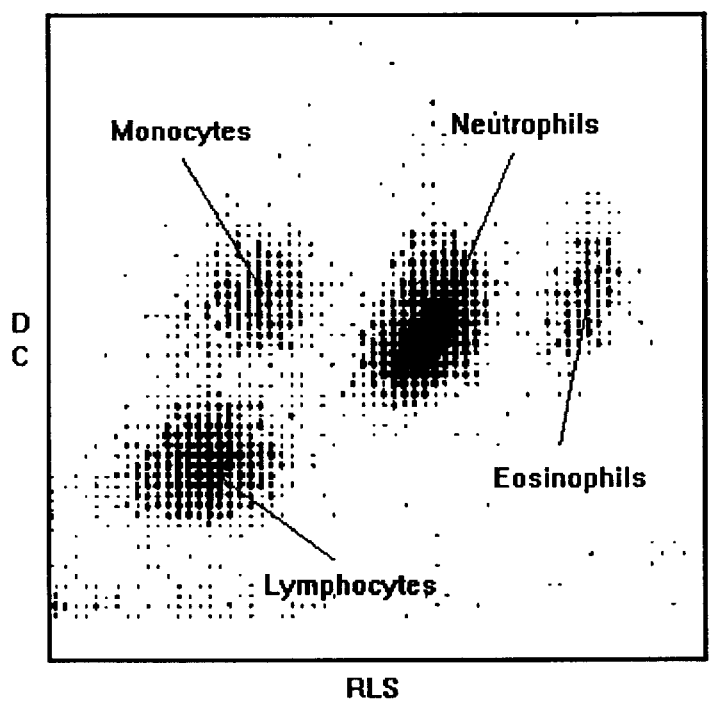
Figure 16:
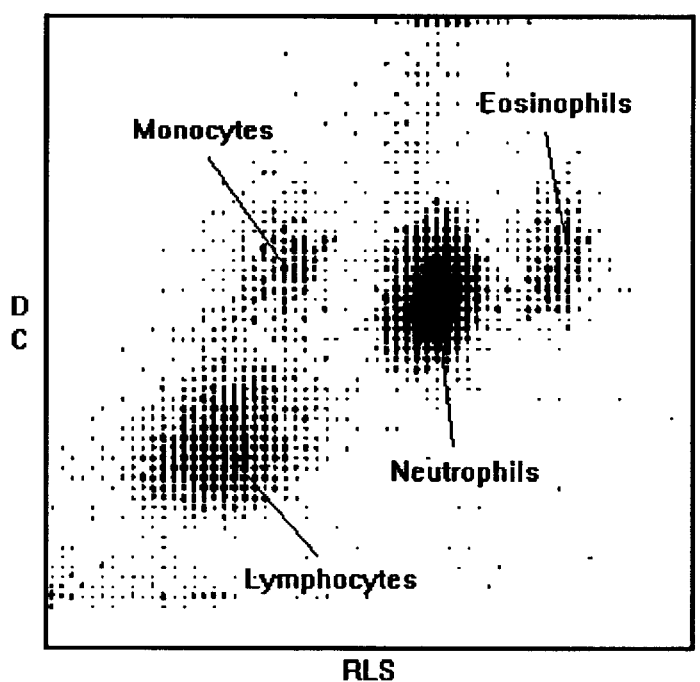

Alternatively, by using a phosphate buffered stabilizing reagent as in Example II to inhibit the lysis reaction and stabilize the leukocytes, good differentiation of the leukocyte subpopulations is obtained. FIG. 14 shows four of the leukocyte subpopulations, including lymphocytes, monocytes, neutrophils and eosinophils.

b) Using the procedure described above with the lytic reagent composition of Example Ib), selective lysis of the red blood cells and differential analysis of leukocyte subpopulations was performed. FIG. 15 shows four leukocyte subpopulations seen with the DC vs. light scatter scattergram obtained from this analysis. A fifth leukocyte subpopulation, basophils, can be obtained by gating the acquired data as described above.

c) Using the procedure described above with the lytic reagent composition of Example Ic), selective lysis of the red blood cells and differential analysis of leukocytes subpopulations was performed. FIG. 16 shows the DC vs. light scatter scattergram obtained from this analysis. This scattergram distinctly shows four of the leukocyte subpopulations including lymphocytes, monocytes, neutrophils and eosinophils. The basophils can be obtained by gating the acquired data as described above.

EXAMPLE IV

Figure 4:
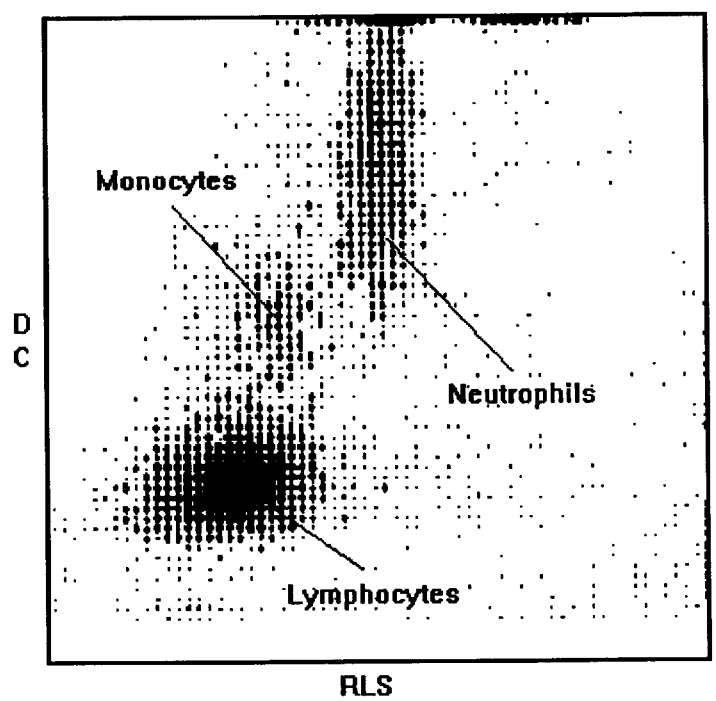
Figure 12:
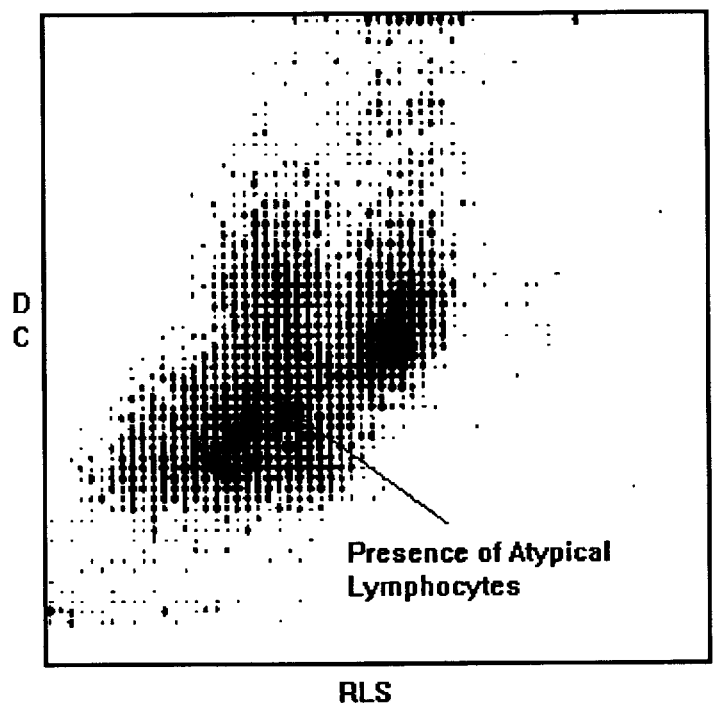
FIGS. 12–14 are scattergrams obtained in accordance with the practice of the present invention as described in Examples III and IV.
Figure 13:
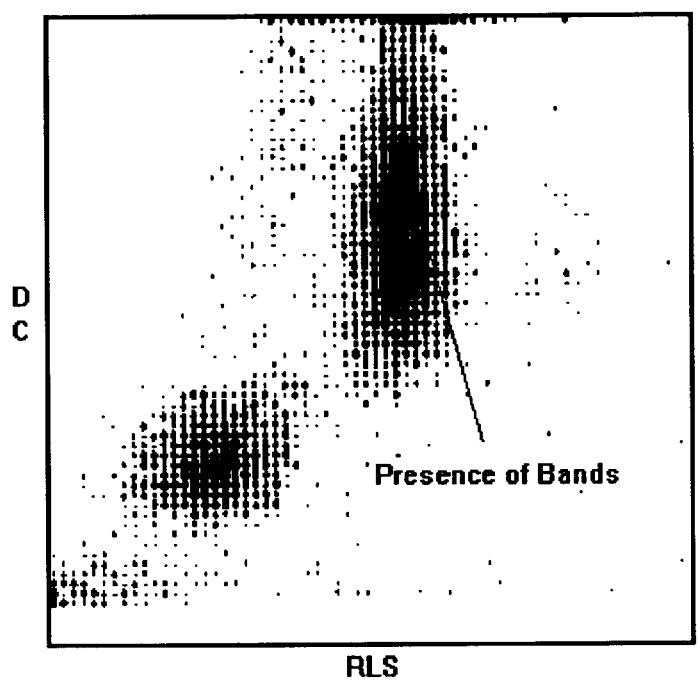

Lysis RBC and Differentiation of Abnormal Human Leukocyte Populations a) The procedure of Example III was repeated for leukocyte differentiation of blood from an active sickle cell patient, using the same reagents as in Example III. It has been commonly seen that active sickle cell blood is difficult to lyse by some commercial hypotonic acid lysing reagents and the subsequent population separation among the leukocyte subpopulations is poor. In these cases, a false differential report can be generated by an automated hematology analyzer. As shown in FIG. 4, a clear population separation indicating the presence of pathology by the abnormality leukocyte differentials was obtained for the active sickle cell blood sample by using the method of this invention.

b) The procedure of Example III was repeated for leukocyte differentiation of blood from a patient having acute lymphocytic leukemia. As seen in FIG. 12, analysis of the blood sample using the method of this invention indicates the presence of atypical lymphocytes.

c) Using the procedure and reagents of Example III, the presence of bands, indicative of immature granulocytes in a blood sample of a patient diagnosed with breast cancer was shown (FIG. 13) to be preserved.

EXAMPLE V

Lysis RBC and Differentiation of Non-Human Animal Leukocyte Populations

Figure 5:
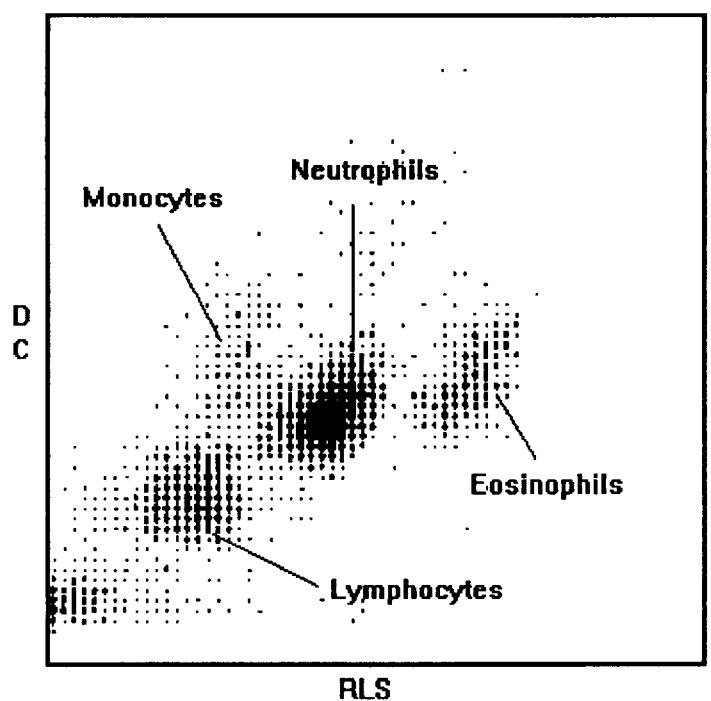
Figure 6:
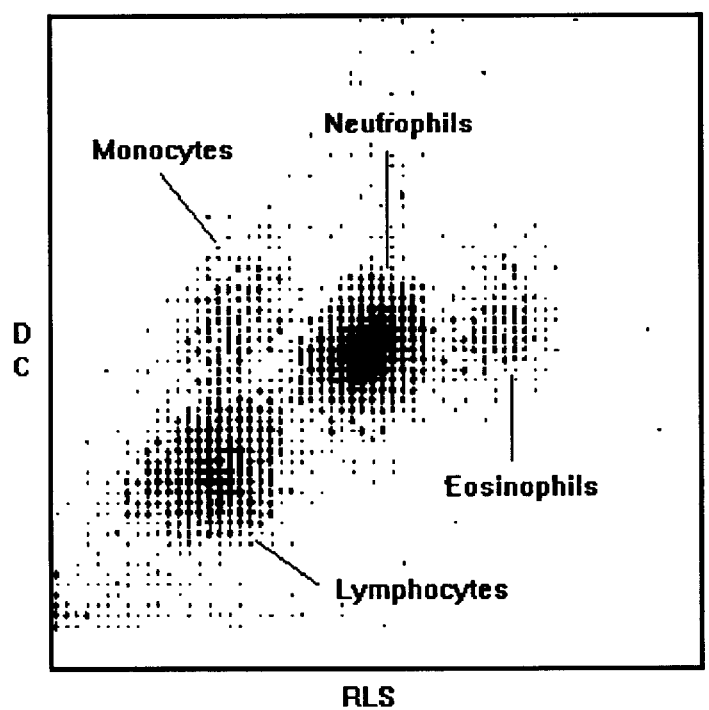
Figure 7:
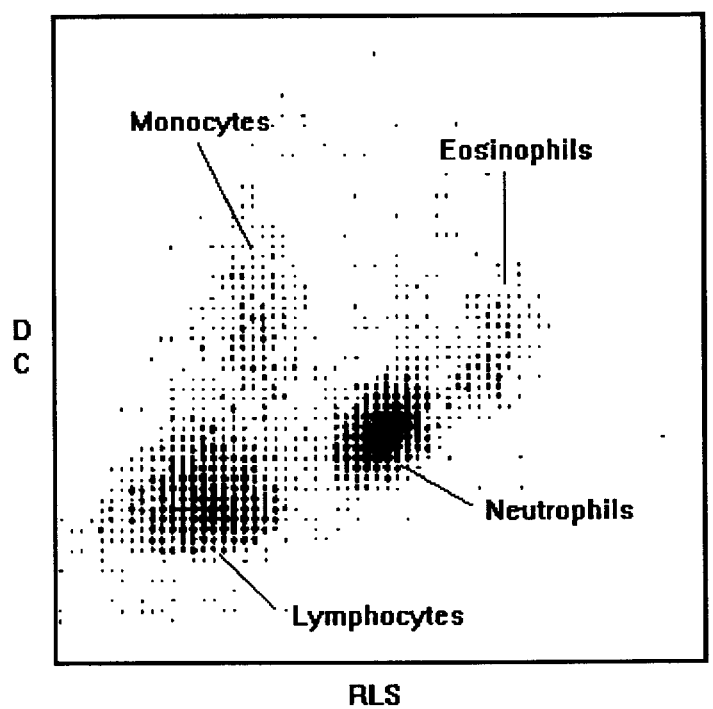
Figure 8:
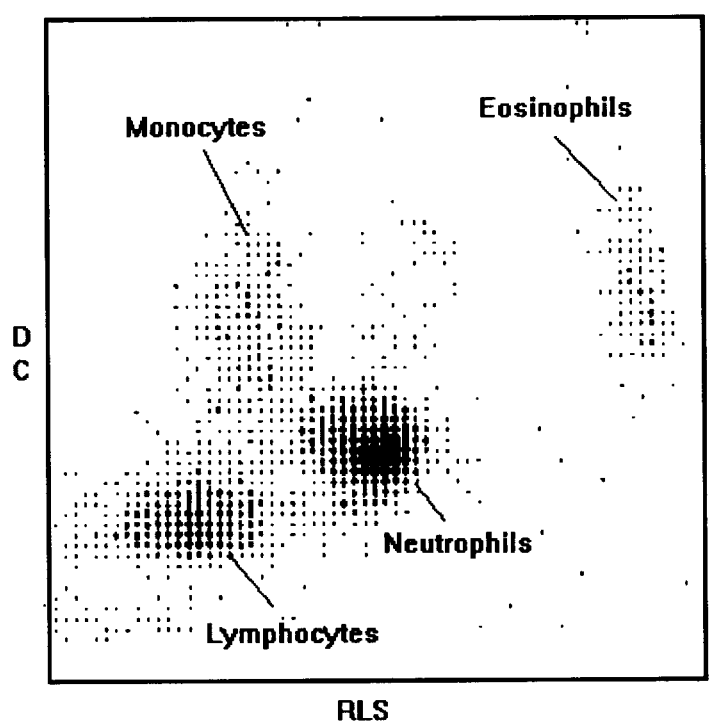
Figure 9:
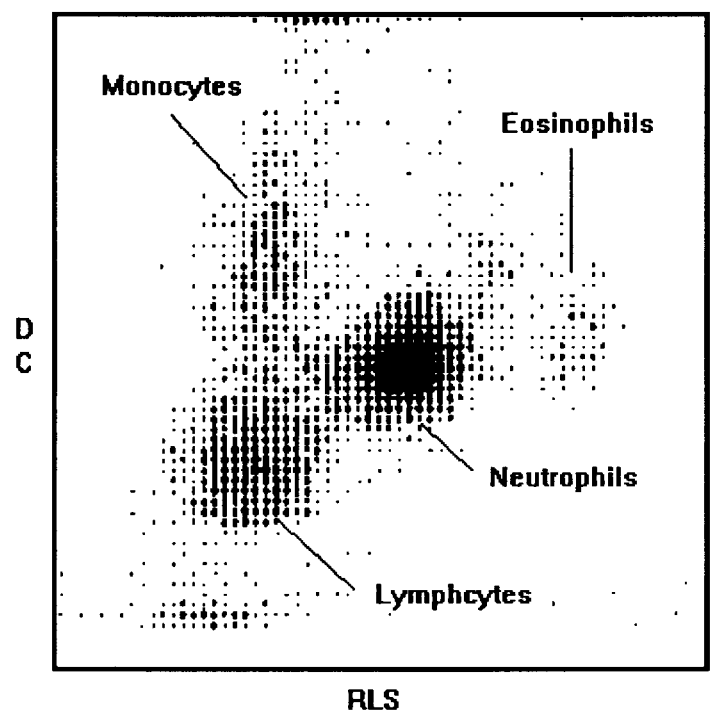

Several veterinary whole blood samples were analyzed using the same method, lytic reagent system described in Example III, except that the lytic reaction time varied among the different species from 2 to 7 seconds and the stabilizing reagent composition interaction time was from 6 to 20 seconds. The lytic reaction times and stabilizing reagent interaction times are consistent between different experiments performed on a given species. The resulting DC vs. light scatter scattergrams are shown in FIGS. 5 to 9 with following order: FIG. 5, canine whole blood sample; FIG. 6, simian whole blood sample; FIG. 7, caprine whole blood sample; FIG. 8, equine whole blood sample and FIG. 9, guinea pig whole blood sample.

As shown by the scattergrams, although each species has its own characteristics in terms of the respective subpopulation distribution, the leukocyte subpopulations including lymphocytes, monocytes, neutrophils and eosinophils within a species, are clearly distinct from each other. Among different species, the lytic reaction time and reagent volume can be varied in order to obtain the best differential results, but such variations can be easily accomplished by automated blood analyzers.

This invention allows, for the first time, an ability to differentiate at least four different subpopulations of leukocytes, i.e., lymphocytes, monocytes, neutrophils and eosinophils, with veterinary whole blood samples utilizing an automated method.

EXAMPLE VI

Figure 10A:
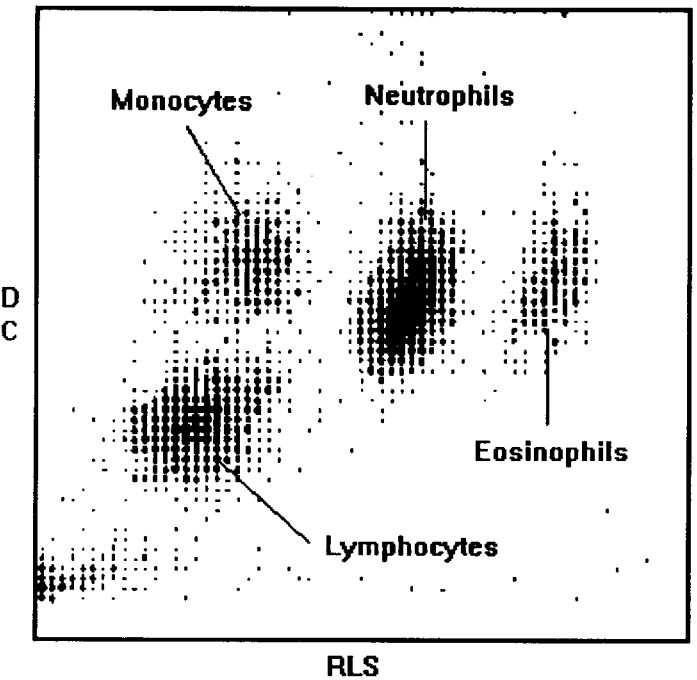
Figure 10B:
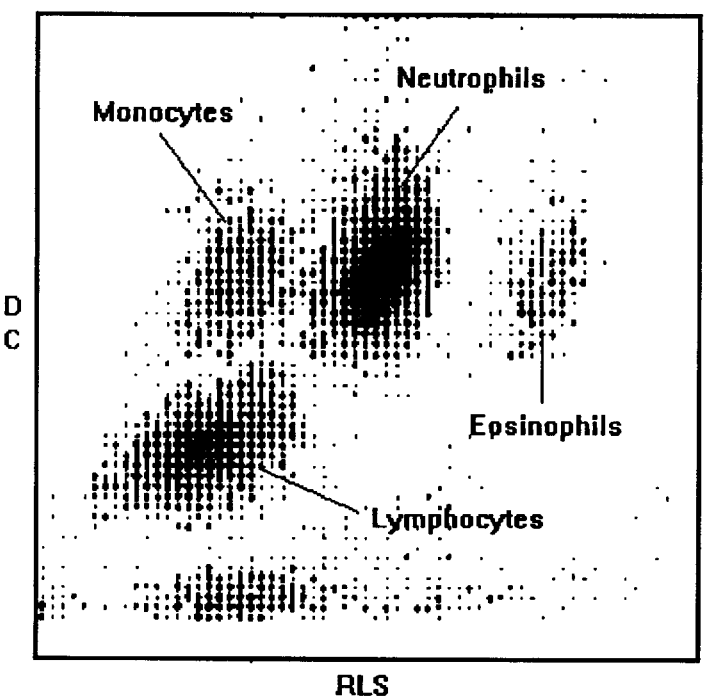

Lysis RBC and Differentiation of Human Leukocyte Populations From Aged Blood Samples The procedure of Example III was repeated utilizing the same lytic reagent system for leukocyte differentials of a whole blood sample several hours after gathering for direct comparison of the differentiation with fresh blood samples. The sample was stored at room temperature, approximately 21° C. As clearly shown in FIG. 10, similar leukocyte subpopulation profiles were obtained for fresh blood, FIG. 10A, and blood samples that were 27 hours old, FIG. 10B, demonstrating that this invention can be used for leukocyte differentiation and analysis several hours after blood sample collection.

EXAMPLE VII

Hemoglobin Concentration Determination of Blood Samples

Figure 11:
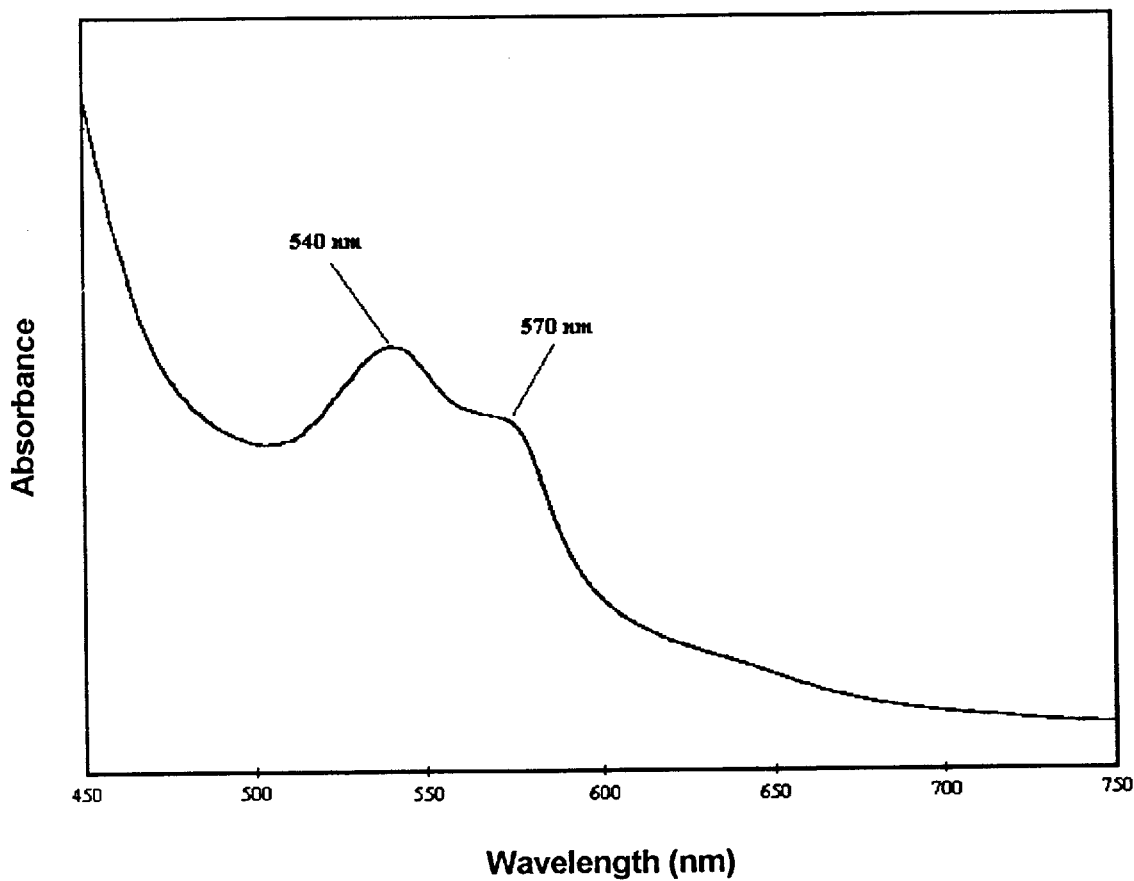
FIG. 11 is a graph illustrating the absorption profile of the sample described in Example VII.

The lytic reagent system of Example III was used in the determination of hemoglobin concentration in whole blood samples. 14 µl of whole blood were mixed with 1224 µl of the lytic reagent composition and gently mixed for 5 to 8 seconds. 498 µl of the stabilizing reagent composition was added and after 10 seconds, an absorption profile of the resulting chromogen was measured. As seen in FIG. 11, the chromogen has a maximum absorption peak at 540 nm with a shoulder at 570 nm. The chromogen formed less than 10 seconds after addition of the stabilizing reagent and was stable for more than 20 minutes.

EXAMPLE VIII

Whole Blood Leukocyte Differentials by Fluorescence

A blood sample is stained with an aqueous dye solution at a 10:1 (blood:dye) ratio for a few minutes. 28 µL of the stained blood sample is aspirated to a hematology analyzer with the same reagent volumes and reaction times to the regular 5-part differential analysis described in Example III. The sample mixture is analyzed by fluorescence and DC. The major populations, i.e., lymphocytes, monocytes, neutrophils and eosinophils, can be clearly separated.

EXAMPLE IX

Selective Lysis and Differential Analysis of Non-Peripheral Fluid Sample

To 14 µl of a non-peripheral fluid sample, bone marrow, approximately 1200 µl of the lytic reagent composition of Example I will be added and the mixture will be gently mixed for about 2 to 7 seconds at room temperature (approximately 21° C.). The lysing reaction will be retarded by the addition of about 490 µl of the stabilizing reagent composition of Example II. The sample mixture will be gently mixed for a few seconds and ready for differential analysis 7 to 18 seconds after the addition of the stabilizing reagent composition. The differential analysis will be conducted on a hematology analyzer described in Example III. The leukocyte subpopulations will be identified and quantified using the scattergrams illustrated in Example III.

EXAMPLE X

Lysis of RBC and Differentiation of Lymphocyte Subpopulations by Flow Cytometer

To 100 µl of a whole blood sample, 10 µl of T8-FITC (fluorochrome labeled antibody) was added. The sample was gently mixed, then incubated at room temperature for 15 minutes.

An aliquot of 34 µl of the incubated blood sample was pipetted into a test tubing. 521 µl of the lytic reagent composition of Example Ia was added and the mixture was mixed by swirling for 4 seconds at room temperature (approximately 21° C.). The lysing reaction was retarded by adding 206 µl of the stabilizing reagent composition of Example IIa. The blood mixture was gently mixed for 5 seconds and analyzed on a COULTER® EPICS® XL flow cytometer using light scatter and fluorescence for CD8 positive lymphocytes.

The same incubated blood sample was also treated by a commercial reagent system, ImmunoPrep, using a blood sample preparation instrument, COULTER Q-Prep EPICS® Immunology Workstation (manufactured by Coulter Corporation). The treated sample was analyzed on the same flow cytometer. The ImmunoPrep reagent system and method comprise a 3-step sample preparation: (1) adding Immunoprep Reagent A, an acid lyse, to a blood sample to lyse red cells; (2) adding Immunoprep Reagent B, a quench solution, to quench the lysing reagent; (3) adding Immuno-Prep Reagent C, a fixative reagent, to fix white cells.

Figure 17:
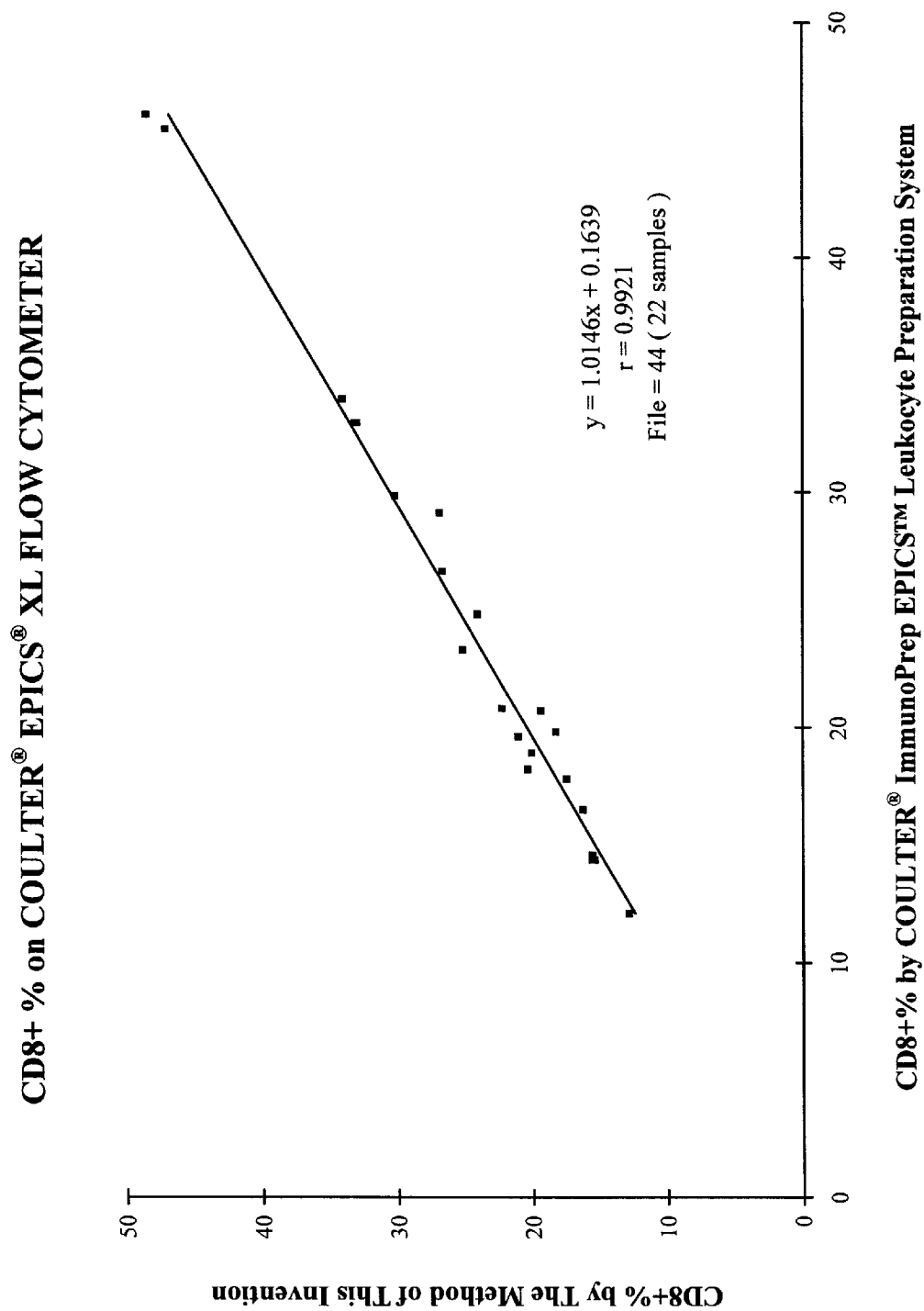
FIG. 17 is a curve illustrating the correlation between results obtained by a reference method and the method of the present invention as described in Example X.

Twenty-two fresh peripheral blood samples were treated and analyzed following the above-described procedure of the present invention. Each blood sample was run in duplicate. The obtained CD8+% results were plotted against the ones obtained from the same samples using the commercial ImmunoPrep method. FIG. 17 shows the correlation between the commercial method and the method of the present invention. The correlation coefficient (0.992), as well as the slope and the intercept of the regression line demonstrate an excellent correlation between the two methods for CD8+%.

EXAMPLE XI

Lysis of RBC and Differentiation of Lymphocyte Subpopulations Using Antibody-Conjugated Particles To 200 µl of a whole blood sample, 20 µl of antibody T4 conjugated latex particles was added. The sample was mixed on a vortex mixer for 2 minutes at room temperature.

Figure 18:
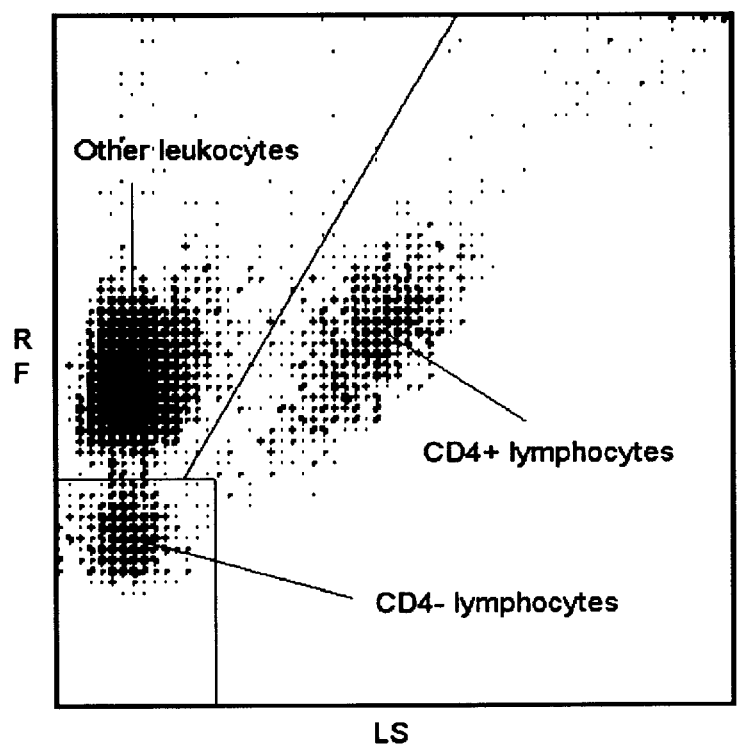
FIG. 18 is a scattergram obtained in accordance with the practice of the present invention as described in Example XI.

An aliquot of 28 µl of the blood sample labelled by antibody-conjugated particles was aspirated into an experimental focus-flow hematology analyzer, equipped with DC, RF and light scatter detection device. 420 µl of the lytic reagent of Example Ia was delivered into a mixing chamber together with the aliquot of blood sample and the mixture was mixed mechanically for 4 seconds at room temperature (approximately 21° C.). 180 µl of the stabilizing reagent of Example IIa was then added into the mixing chamber and the sample mixture was mixed to retard the lytic reaction. The blood mixture was analyzed in a flow cell by DC, RF and light scatter measurements for leukocyte differentiation and analysis of CD4 positive (CD4+) lymphocytes. FIG. 18 shows a scattergram for differentiation of CD4 positive lymphocytes. The CD4 positive lymphocytes bound to the T4 antibody conjugated latex particles showed a shift on light scatter signals on a RF vs. light scatter scattergram. The CD4 positive lymphocytes formed a distinct cluster and separated from the CD4 negative lymphocyte populations and other leukocytes. The CD4+% results obtained using the method of the present invention are consistent with those obtained using conventional fluorescent flow cytometry.

The invention has been described with reference to particularly preferred embodiments. It will be appreciated, however, that various changes can be made without departing from the spirit of the invention, and such changes are intended to fall within the scope of the appended claims.

What is claimed is:

1. A method for counting white blood cells (WBC), determining hemoglobin concentration, and differentiating at least four subpopulations of leukocytes in a blood cell sample comprising:

(a) exposing a blood cell sample to a lytic reagent for a time sufficient to lyse red blood cells without heating said exposed blood cell sample;

(b) adding a non-aldehyde stabilizing reagent to said exposed blood sample, wherein said stabilizing reagent inhibits further lytic action and stabilizes leukocytes without fixing the leukocytes;

(c) converting oxyhemoglobin to a stable hemoglobin chromogen in said stabilized sample;

(d) analyzing said stabilized sample in less than 30 seconds after addition of the lytic reagent, wherein a mode of analzing is selected from at least two modes selected from the group consisting of DC, RF, and light scatter, wherein said analyzing is for counting WBC, and differentiating at least four leukocyte subpopulations selected from the group consisting of lymphocytes, monocytes, basophils, neutrophils and eosinophils;

(e) measuring light absorbance of said stabilized sample at about 540 nm for determination of hemoglobin concentration; and (f) reporting WBC, hemoglobin concentration and at least four leukocyte subpopulations.

2. The method of claim 1, wherein said time sufficient to lyse red blood cells is less than 10 seconds.

3. The method of claim 1, wherein said hemoglobin concentration measurement method is a non-cyanide method.

4. The method of claim 1, wherein reporting of said leukocyte subpopulations is in absolute count or percentage.

5. The method of claim 1, wherein said blood cell sample includes peripheral blood of a human, peripheral blood of a non-human, bone marrow of a human, bone marrow of a non-human, an indicator-labeled whole blood of a human or a non-human, or an indicator-labeled bone marrow of a human or a non-human.

6. A method for stromatolysis of red blood cells in a blood cell sample, analysis of leukocyte subpopulations and lymphocyte subpopulations, and determining hemoglobin concentration in the blood cell sample comprising:
   (a) incubating a blood cell sample with a fluorochrome-conjugated antibody for analysis of lymohocyte subpopulations;
   (b) exposing the incubated blood cell sample to a lytic reagent for a time sufficient to lyse red blood cells without heating said exposed blood cell sample;
   (c) adding a non-aldehyde stabilizing reagent to said exposed blood cell sample, wherein said stabilizing reagent inhibits further lytic action and stabilizes leukocytes of said blood cell sample in a hypertonic medium ranging from about 400 mOsm to about 600 mOsm without fixing the leukocytes;
   (d) converting oxyhemoglobin to a stable hemoglobin chromogen in said stabilized sample;
   (e) analyzing said stabilized sample in less than 30 seconds after addition of the lytic reagent, wherein a mode of analyzing is selected from at least two modes selected from the group consisting of DC, RF, light scatter and fluorescence, wherein said analyzing is for differentiating leukocyte subpopulations and lymphocyte subpopulations;
   (f) measuring light absorbance of said stabilized sample at about 540 nm for determination of hemoglobin concentration;
   (g) reporting leukocyte subpopulations and lymphocyte subpopulations in said blood cell sample; and
   (h) reporting hemoglobin concentration of said blood cell sample.

7. The method of claim 6 which further comprises analyzing for white blood cells (WBC) and reporting WBC of said blood cell sample.

8. The method of claim 6, wherein said time sufficient to lyse red blood cells is less than 10 seconds.

9. The method of claim 6, wherein said leukocyte subpopulations and lymphocyte subpopulations are selected from the group consisting of lymphocytes, T-lymphocytes, B-lymphocytes, monocytes, neutrophils, eosinophils, and basophils.

10. The method of claim 6, wherein reporting of said leukocyte subpopulations is in absolute count or percentage.

11. The method of claim 6, wherein said blood cell sample includes peripheral blood of a human, peripheral blood of a non-human, bone marrow of a human, or bone marrow of a non-human.

12. A method for stromatolysis of red blood cells in a blood cell sample, analysis of leukocyte subpopulations and lymphocyte subpopulations, and determining hemoglobin concentration in the blood cell sample comprising:
   (a) incubating a blood cell sample with antibody-conjugated latex particles for analysis of lymphocyte subpopuations;
   (b) exposing the incubated blood cell sample to a lytic reagent for a time sufficient to lyse red blood cells;
   (c) adding a non-aldehyde stabilizing reagent to said exposed blood cell sample, wherein said stabilizing reagent inhibits further lytic action and stabilizes leukocytes of said blood cell sample without fixing the leukocytes;
   (d) converting oxyhemoglobin to a stable hemoglobin chromogen in said stabilized sample;
   (e) analyzing said stabilized sample in less than 30 seconds after addition of the lytic reagent, wherein a mode of analyzing is selected from at least two modes selected from the group consisting of DC, RF, light scatter and fluorescence, wherein said analyzing is for differentiating leukocyte subpopulations and lymphocyte subpopulations;
   (f) measuring light absorbance of said stabilized sample at about 540 nm for determination of hemoglobin concentration;
   (g) reporting leukocyte subpopulations and lymphocyte subpopulations in said blood cell sample; and
   (h) reporting hemoglobin concentration of said blood cell sample.

13. The method of claim 12, wherein said time sufficient to lyse red blood cells is less than 10 seconds.

14. The method of claim 12, wherein said hemoglobin concentration measurement method is a non-cyanide method.

15. The method of claim 12, wherein said leukocyte subpopulations and lymphocyte subpopulations are selected from the group consisting of lymphocytes, T-lymphocytes, B-lymphocytes, monocytes and granulocytes.

16. The method of claim 12, wherein reporting of said leukocyte subpopulations is in absolute count or percentage.

17. The method of claim 12, wherein said blood cell sample includes peripheral blood of a human, peripheral blood of a non-human, bone marrow of a human, or bone marrow of a non-human.

* * * * *